United States Patent
KraMer et al.

(10) Patent No.: US 8,251,947 B2
(45) Date of Patent: Aug. 28, 2012

(54) TWO-STAGE RECONSTITUTING INJECTOR

(75) Inventors: Thomas E. KraMer, Coon Rapids, MN (US); Peter L. Sadowski, Woodbury, MN (US)

(73) Assignee: Antares Pharma, Inc., Minneapolis, MN (US)

( * ) Notice: Subject to any disclaimer, the term of this patent is extended or adjusted under 35 U.S.C. 154(b) by 549 days.

(21) Appl. No.: 12/299,274

(22) PCT Filed: May 2, 2007

(86) PCT No.: PCT/US2007/067986
§ 371 (c)(1),
(2), (4) Date: Jun. 3, 2009

(87) PCT Pub. No.: WO2007/131013
PCT Pub. Date: Nov. 15, 2007

(65) Prior Publication Data
US 2009/0292240 A1    Nov. 26, 2009

Related U.S. Application Data

(60) Provisional application No. 60/796,939, filed on May 3, 2006.

(51) Int. Cl.
*A61M 37/00* (2006.01)
(52) U.S. Cl. ......................................................... 604/82
(58) Field of Classification Search ....... 604/82
See application file for complete search history.

(56) References Cited

U.S. PATENT DOCUMENTS

| | | | | |
|---|---|---|---|---|
| 4,529,403 | A | * | 7/1985 | Kamstra .................. 604/136 |
| 6,171,276 | B1 | * | 1/2001 | Lippe et al. .................. 604/67 |
| 2005/0080377 | A1 | * | 4/2005 | Sadowski et al. .............. 604/131 |

FOREIGN PATENT DOCUMENTS

| | | |
|---|---|---|
| EP | 0 072 057 | 2/1983 |
| EP | 1 518 575 A1 | 3/2005 |
| WO | WO 94/09839 | 5/1994 |

OTHER PUBLICATIONS

International Search Report PCT/US2007/067986 Dated Sep. 27, 2007.

* cited by examiner

*Primary Examiner* — Nicholas Lucchesi
*Assistant Examiner* — Jason Flick
(74) *Attorney, Agent, or Firm* — Morgan, Lewis & Bockius LLP

(57) ABSTRACT

An injector for injecting a medicament into a patient. The injector includes a container defining a first chamber, which contains a fluid therein, and a second chamber. The injector also includes an injection conduit configured for directing the fluid fired from the container into the patient. A transfer mechanism is operable by a user to transfer the fluid from the first chamber to the second chamber in a first stage of operation, and a firing mechanism is operable by the user for firing the fluid from the second chamber through the injection conduit in a second stage of operation. An energy source is in powering association with the firing mechanism to drive firing mechanism in the first and second stages.

33 Claims, 4 Drawing Sheets

TWO-STAGE RECONSTITUTING INJECTOR

This application is a 371 filing of International Patent Application PCT/US2007/067986 filed May 2, 2007, which claims the benefit of application No. 60/796,939 filed May 3, 2006.

FIELD OF THE INVENTION

The present invention relates to an injector, and more particularly to an injector in which materials from at least two compartments are contained before the injection is made.

BACKGROUND OF THE PRESENT INVENTION

Known injection devices for injection of medicaments into a patient include traditional hypodermic needle syringes, needle-free jet injectors like the ones disclosed in U.S. Pat. Nos. 5,599,302; 5,062,830; and 4,790,824; needle-assisted injectors, such as those described in U.S. Patent Publication No. 2005/0033234; and self-injectors or autoinjectors like the ones disclosed in U.S. Pat. Nos. 4,553,962 and 4,378,015, and PCT Publications WO 95/29720 and WO 97/14455.

The liquid medicament preparations that are injected from such injection devices are also known to contain insoluble or particulate drug constituents. This can be due to the insolubility of the drug in the vehicle or medium in which it is stored. As a result, the insoluble or particulate drug constituents in the liquid preparations separate upon storage, even over short periods of time.

The particulates can potentially clog the needle, and this is particularly problematic in cases when the liquid pharmaceutical preparation containing insoluble particles is self-administered or administered in the home by non-professional caregivers. Ordinarily, when these liquid pharmaceutical preparations are administered in the hospital or other healthcare providing institutions by trained staff, one can rely on adequate handling of the medication to ensure proper drug delivery, despite settled material and plugged needles. However when such pharmaceutical preparations are self-administered or administered in the home by non-professional caregivers, the risk for inadequate handling of the medication increases since the injection of such formulations requires that the administrator be able to adequately resuspend any settled material and clear the needle to ensure proper drug delivery.

Thus, an injector is needed that can facilitate reliable combination of injectable components prior to injection.

SUMMARY OF THE INVENTION

The invention is related to an injector for injecting a medicament into a patient. The preferred embodiment of the injector includes a container defining a first chamber containing a fluid therein, and a second chamber. An injection conduit is configured for directing the fluid fired from the container into the patient. The injector also includes a transfer mechanism operable by a user to transfer the fluid from the first chamber to the second chamber in a first stage of operation, and a firing mechanism operable by the user for firing the fluid from the second chamber through the injection conduit in a second stage of operation. An energy source is in powering association with the firing mechanism to drive firing mechanism in the first and second stages.

Preferably, the injector also includes a transfer control that is manually operable to operate the injector in the first stage of operation. The first stage preferably also includes venting the second chamber. The injection conduit preferably has a position that is initially fluidly incommunicated with the second chamber, and the transfer control preferably operates the transfer mechanism in the first stage of operation and fluidly communicates the injection conduit with the second chamber in the first stage of operation. Preferably, the transfer control includes a cap associated with the container and disposed to cover the injection conduit prior to the first stage of operation. Also, the cap is preferably separable from the injection conduit and container after the first stage of operation. Preferably, the injector includes a cap release in locking association with the cap to prevent operation thereof. The cap release is positionable in a release position in which the cap release releases the cap to permit operation thereof in the first stage of operation.

The injection conduit preferably includes a communicating needle portion, and the transfer control is operable to relatively move the communicating needle portion with respect to the second chamber to pierce the container to fluidly communicate the second chamber with the communicating needle portion in the first stage of operation. The injection conduit also preferably includes an injecting needle portion disposed and configured to pierce the skin of the patient for assisting the injection of the fluid in the second stage.

Preferably, the energy source and firing mechanism are configured for delivering the fluid in a jet to an injection site within the patient tissue remote from the injecting needle. The injection conduit preferably includes a jet nozzle disposed and configured to deliver the fluid in a jet into the patient during the second stage of operation to pierce the skin of the patient for assisting the injection of the fluid in the second stage.

Preferably, the second chamber comprises the medicament, and the fluid in the first chamber is a diluent configured for dissolving or suspending the medicament therein for injection into the patient. The energy source is preferably associated to power the transfer mechanism to transfer the fluid to the second chamber. The preferred injector also includes an injection trigger mechanism operably associated with the firing mechanism to operate the firing mechanism in the second stage. The transfer and firing mechanisms can include a firing ram that is movable over a first throw in the first stage of operation and a second throw in the second stage of operation, the energy source in biasing association with the ram in each stage of operation to power the ram. The injection trigger mechanism is configured to block movement of the ram beyond the first throw, the injection trigger being actuatable to release the ram to travel over the second throw.

The injector also preferably includes a retractable guard that is movable between a protecting position in which the injection conduit is disposed within the guard, and an injecting position in which an injection needle portion of the injection conduit is exposed for injection of the fluid in the patient. Preferably, the injection trigger mechanism is configured for operating the firing mechanism in the second stage after the retractable guard is retracted from the protecting position. Also, the retractable guard can be operably associated with the injection trigger mechanism to cause the injection trigger mechanism to operate the firing mechanism when the guard is retracted to the injecting position.

In another preferred embodiment, the injector includes a container that includes a fluid chamber containing a medicament therein, the fluid chamber comprising a needle hub at the distal end thereof, and an injection conduit configured for directing the medicament fired from the container into the patient, the injection conduit having a position that is fluidly incommunicated with the fluid chamber. The injector also includes a transfer control operable to fluidly communicate the injection conduit with the needle hub of the fluid chamber. The transfer control includes a cap associated with the container and disposed to cover the injection conduit, the cap being separable from the injection conduit upon operating the transfer control to fluidly communicate the injection conduit with the needle hub.

Preferably, the injection conduit includes a communicating needle portion, the transfer control being operable to relatively move the communicating needle portion with respect to the fluid chamber to pierce the container adjacent the needle hub to fluidly communicate the fluid chamber with the communicating needle portion.

A trigger device can be associated with the energy source and the firing mechanism, with the triggering device being operable in a first triggering stage, which causes the firing mechanism to operate in the first stage of operation. The triggering device can be configured such that only after the firing mechanism has operated in the first stage of operation, the triggering device is operable in a second triggering stage which causes the firing mechanism to operate in the second stage of operation. The triggering device can have a single control that is operable in the first and second triggering stages, or separate controls to operate in each of the first and second triggering stages.

The present invention thus provides an injector that enables reconstitution of a liquid medicament preparation, preferably just prior to injection, to enable easy and effective delivery of the medicament to a patient.

DETAILED DESCRIPTION OF THE PREFERRED EMBODIMENTS

Figure 1:
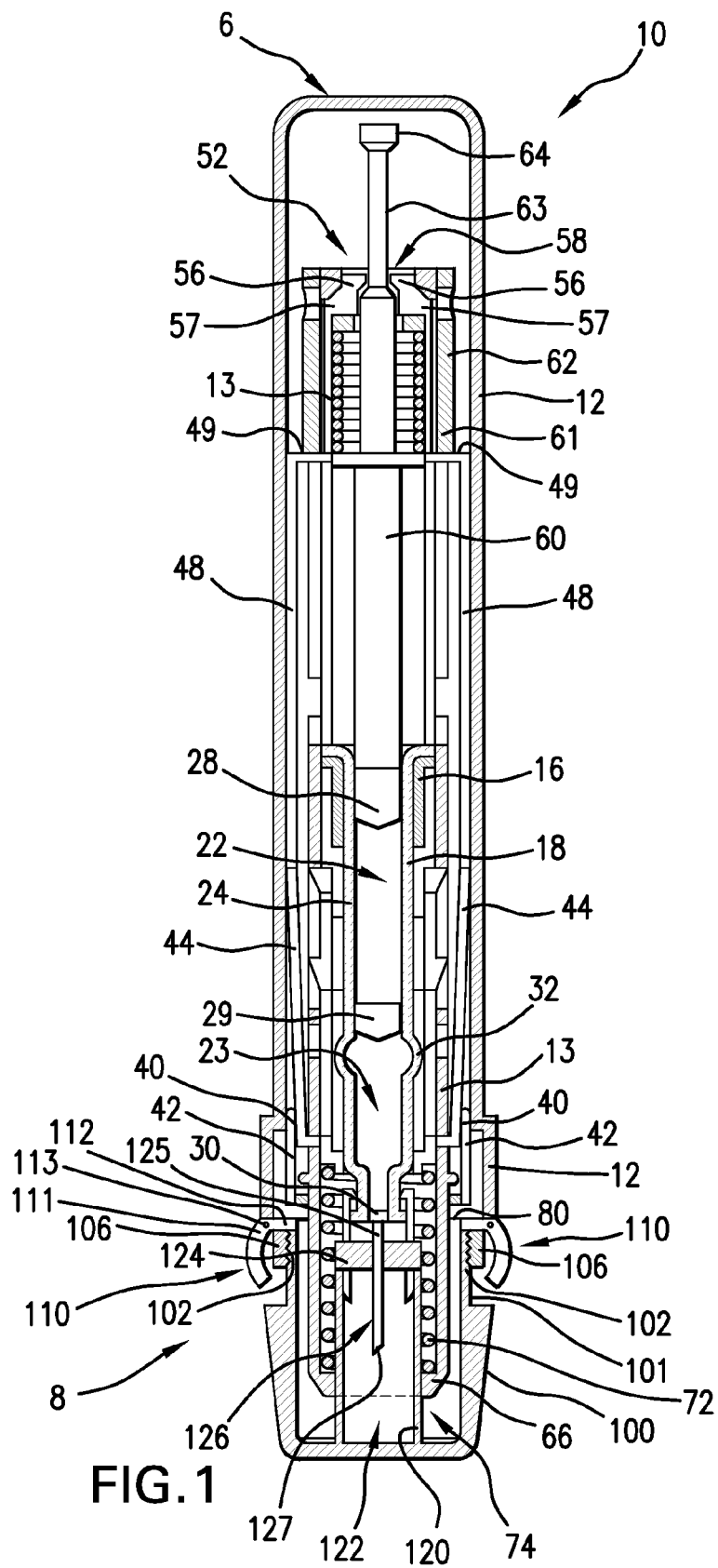
FIG. 1 is a cross-sectional view of a preferred embodiment of an injector constructed according to the present invention, showing the injector with a cap associated therewith.

Referring to FIG. 1, a preferred embodiment of an injector 10 has a tubular outer housing 12 having a proximal end 6 and a distal end 8, and configured for allowing a user to handle the injector 10 and position the injector near or adjacent an injection location of a patient. The outer housing 12 preferably houses most of the components of the injector 10.

Figure 2:
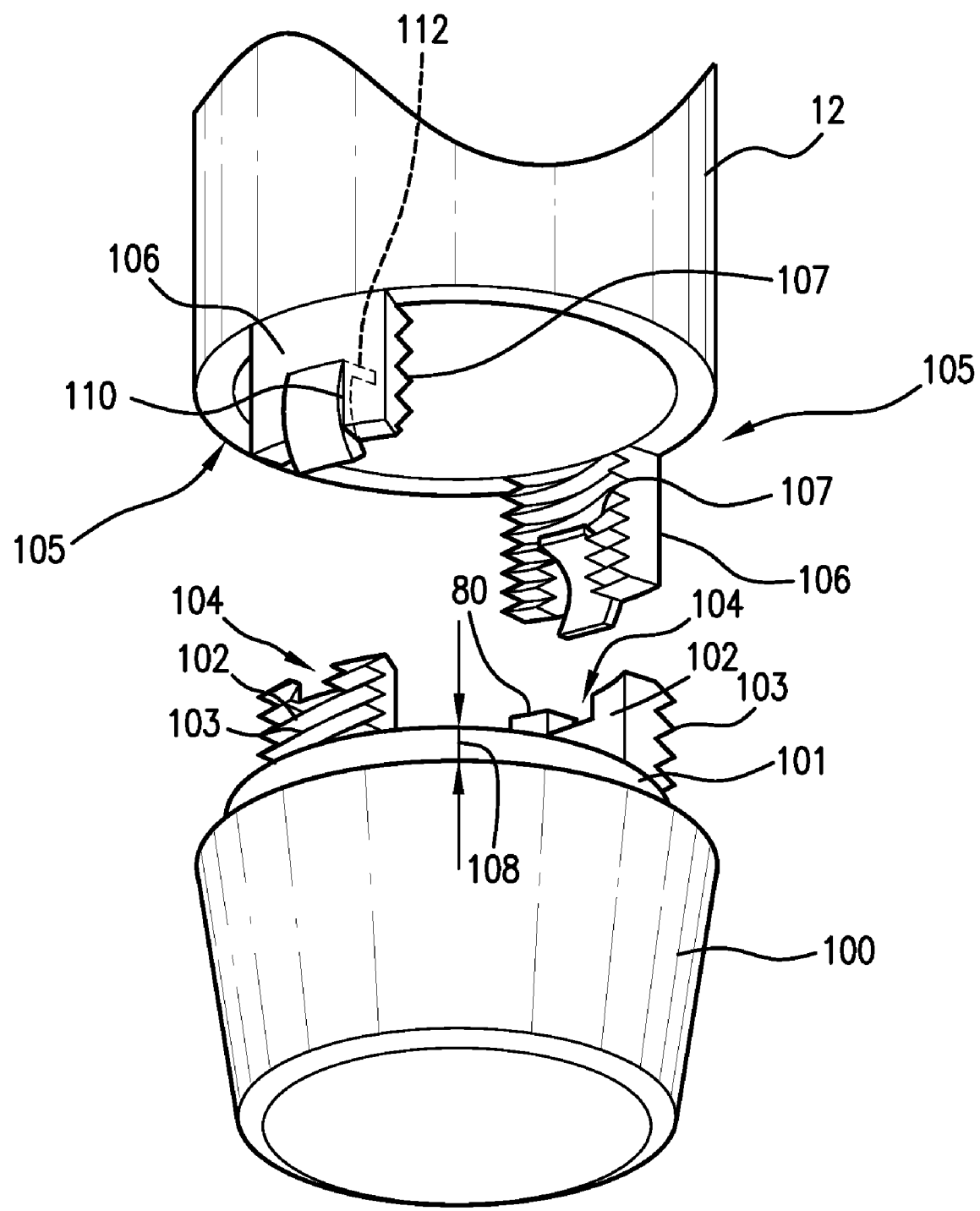
FIG. 2 is a perspective view of the distal end of the housing thereof, with the cap removed.

A cap 100 is associated with the outer housing 12 at the distal end 8 and is configured for covering an injection conduit, which can be a needle 126, or a jet nozzle, for example. The cap 100 preferably includes engagement portions configured for removable engagement with outer housing 12. As shown in the preferred embodiment of FIGS. 1 and 2, the cap 100 preferably includes a radially recessed neck 101 extending a distance 108 from the proximal end thereof. The neck 101 preferably has a smaller diameter than the remaining portion of the cap 100, but can have the same or larger diameter in other embodiments. A pair of engagement portions 102 extend preferably proximally towards the outer housing 12 from the neck 101, such as on opposing sides there. Each of the engagement portions 102 preferably extends circumferentially around less than about a quarter, and more preferably less than about a fifth, of the total circumference of the neck 101. The outer radial surface of the engagement portions 102 is preferably a threaded surface 103 configured for threadably associating with a portion of the outer housing 12. The engagement portions 102 also preferably include a notch 104 at the proximal end thereof and which is configured for associating with another portion of the outer housing 12.

The distal end of the outer housing 12 also preferably includes engagement portions 106 configured for removable engagement with the cap 100. Engagement portions 106 extend distally from positions to engage the cap engagement portions 102, and in this embodiment are disposed diametrically opposite sides of the distal end 8 of the outer housing 12. Similar to the engagement portions 102 of the cap 100, the engagement portions 106 of the outer housing 12 preferably extend circumferentially around less than about a quarter, and more preferably less than about a fifth, of the total circumference of the distal end 8 of the outer housing 12. The inner radial surface of the engagement portions 106 is preferably a threaded surface 107. Additionally, the engagement portions 106 preferably define a pair of gaps 105 therebetween, the circumferential length of the gaps 105 preferably larger than the circumferential length of the engagement portions 102 of the cap 100.

Preferably, the width between circumferentially adjacent engagement portions 106 of the outer housing 12 is greater than the width between engagement portions 102 of the cap 100, such that when the cap 100 and outer housing 12 are engaged with each other as shown in FIG. 1, the threaded surface 103 of the engagement portions 102 are in threaded association with the threaded surface 107 of the engagement portions 106, with the engagement portions 102 disposed radially inward with respect to the engagement portions 106.

One or both of the engagement portions 106 preferably further includes a cap lock mechanism 110 that is moveable between a blocking position and a release position. The cap lock mechanism 110 includes an actuation portion 111 that is operable by the user, a blocking portion 112, and a pivot 113 that is mounted preferably to the outer housing 12. When the engagement portions 102 and 106 are in threaded association with each other such that the cap 100 and the outer housing 12 are engaged, each cap lock mechanism 110 is resiliently biased to the blocking position such that each blocking portion 112 is disposed within respective notches 104. In this position, the blocking portion 112 prevents rotation of the cap 100 with respect to the outer housing 12, at least in a direction that would allow cap release, and preferably in both directions. Movement of the cap 100 in the proximal direction with respect to the outer housing 12 is also thus prevented. Actuation of the cap lock mechanism 110, for example, by depressing the actuation portion 111 radially inward, causes the blocking portion 112 to pivot proximally about pivot 113 to a release position. As a result, the blocking member 112 pivots out of association with the notch 104 to a position in which rotation in a cap release direction is permitted, and no longer prevents or obstructs movement of the cap 100 in the proximal direction with respect to the outer housing 12. Preferably, the actuation portion 111 is a button, although it can be any other suitable actuation member in other embodiments, and alternative mechanisms can be used to lock the cap in a protective position. In other embodiments, the cap lock mechanism can be mounted on the cap and be disengageable with notches located on the engagement portions of the outer housing.

The interior of the cap 100 preferably includes a hub-engagement portion 120, which is preferably substantially annular, that defines a holding area 122 therein. The hub-engagement portion 120 is preferably configured for reception in axial opening 74 of guard 66 of the injector 10. Releasably mounted within the holding area 122 is a needle hub 124 to which an injection needle 126, or other injection conduit, is mounted. In a needle-free embodiment, a jet nozzle can be mounted thereto. The needle hub 124 preferably is in a snap-lock association with the holding area 122 of the cap 100, but alternatively can be abutting the cap for free removal therefrom. The needle 126 preferably includes a piercing end 125 and an injection end 127 that terminates in an injection tip. The injection end 127 is preferably configured as known in the art to penetrate the tissue of a patient, preferably the skin, at the injection location. A needle bore extends through the needle 126 forming a conduit for the medicament. Preferably, the needle hub 124 is attached to the needle 126 so that the piercing end 125 is oriented proximally, and the injection end 127 is oriented distally, with respect to the outer housing 12.

In other embodiments, the cap and distal end of the housing can have different configurations for allowing removable engagement therebetween. For example, the cap and housing can include associable bayonet fittings, latch fittings, snap fittings, or other suitable attachment structures.

The injector 10 also includes container support member 16 housed within and mounted with the inner housing 13. The container support member 16 is configured to hold and position a container within the injector 10. The container can be, for example, a cartridge 18 or any other suitable container for holding medicament therein. In the preferred embodiment, the container support member 16 is substantially fixed to the inner housing 13, such as by snaps, an adhesive, a weld, or another known attachment, but may be mounted therein in other manners.

The cartridge 18 preferably includes a container portion 24 that defines in its interior a diluent chamber 22, which is preferably prefilled with a liquid diluent, and a medicament or drug chamber 23, which is preferably prefilled with a particulate drug. The container portion 24 is preferably tubular or cylindrical in shape. The diluent chamber 22 is preferably aligned with and disposed proximally with respect to the medicament chamber 23. Additionally, the diluent chamber 22 is defined by a first plunger 28 at the proximal end of the chamber, a second plunger 29 at the distal end of the chamber, and by the wall of the container portion 24. Similarly, the medicament chamber 23 is defined by the second plunger 29 at the proximal end of the chamber, a membrane, septum 30, or stopper at the distal end of the chamber, and by the wall of the container portion 24. The distal end of the medicament chamber 23, adjacent the septum 30, is preferably configured for engagement and mounting of the needle hub 124 therewith.

A preferred material for the container portion 24 is glass, for example, borosilicate glass that is compatible with most medicaments, but other suitable materials can be used in other embodiments. The first and second plungers or stoppers 28, 29, and the septum 30 seal the respective contents of diluent chamber 22 and medicament chamber 23 therein.

The container 18 also preferably includes a by-pass or a reconstitution bulge 32 where the walls of the container are flared radially outward along a longitudinal length thereof. As such, the radial diameter of the reconstitution bulge 32 is preferably substantially larger than the remaining portions of the container 18. Preferably, the radial diameter and the longitudinal length of the reconstitution bulge 32 is also substantially larger than that of the second plunger 29. The reconstitution bulge 32 is preferably located within the medicament chamber 23 before the injection is commenced or the contents of the diluent and medicament chambers are combined.

Figure 3:
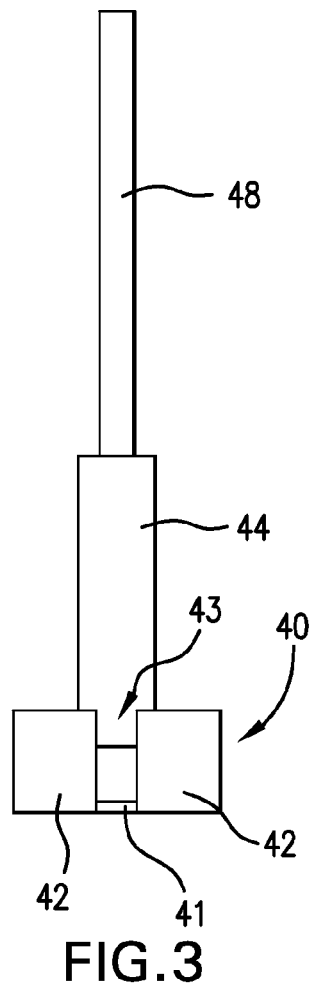
FIG. 3 is a side view of a flex arm, flex arm cam, and an outer sleeve arm of the injector of FIG. 1.

The injector 10 also preferably includes a flex arm cam member 40, flex arms 44, and ram arms 48 contained within the outer housing 12, as shown in FIG. 1. FIG. 3 shows a side view of the relationship between such components. The flex arm cam member 40 is preferably disposed near the distal end of the outer housing 12 such that base 41 of the flex arm cam member 40 is proximally adjacent the cap 100. The flex arm cam member 40 also includes flex arm cams 42 that extend proximally from the base 41 to adjacent a distal portion of one of the flex arms 44. The flex arm cams 42 also define a slot 43 therebetween configured for receiving a portion of the ram arm 48.

The distal end of the of the flex arm 44 can be mounted to inner housing 13 or another suitable portion of the injector 10. The distal portion of the flex arms 44 are disposed radially inward with respect to the flex arm cams 42. The flex arms 44 extend proximally from the flex arm cams 42. The flex arms 44 are shown in a blocking position in FIG. 1. The flex arms 44 are preferably made of a resilient, flexible material such that the proximal ends of the flex arms 40 can flex radially inward upon application of a force thereto to assume a release position.

In the blocking position, the proximal ends of each flex arm 44 is disposed in longitudinal abutment with, and preferably in substantial longitudinal alignment with, the distal end of a respective ram arm 48. The ram arms 48 further extend proximally therefrom to respective shoulders 49, which extend radially inward from each ram arm 48. Preferably, the shoulder 49 is attached to ram 60, which is associated with and biased by an energy source, which in the embodiment of FIG. 1 is a compression spring 62, although other suitable energy sources can alternatively be used such as elastomer, compressed-gas springs, or gas generators. A preferred type of compression spring is a coil spring. As a result, the ram arms 48 are also biased distally by the spring 62, and thus the distal end of each ram arm 48 is biased against the proximal end of each flex arm 44 when the flex arms are in the blocking position. The distal end of the ram 60 is disposed adjacent the proximal end of the first plunger 28. Although the ram 60 is biased distally against the first plunger 28 by the spring 62, the ram 60 is prevented from displacing the first plunger 28 because the ram arms 48 are blocked by the flex arms 44.

The ram 60 also includes a proximal portion that includes a shaft 63 and terminates proximally at enlarged portion or end 64. The enlarged end 64 preferably has a radial diameter that is substantially greater than that of the shaft 63, and which is also too large to fit through aperture 58 between the trigger protrusions 56, which thus prevents or impedes distal movement of the ram 60 past where the trigger protrusions 56 would abut the enlarged end 64.

Figure 4:
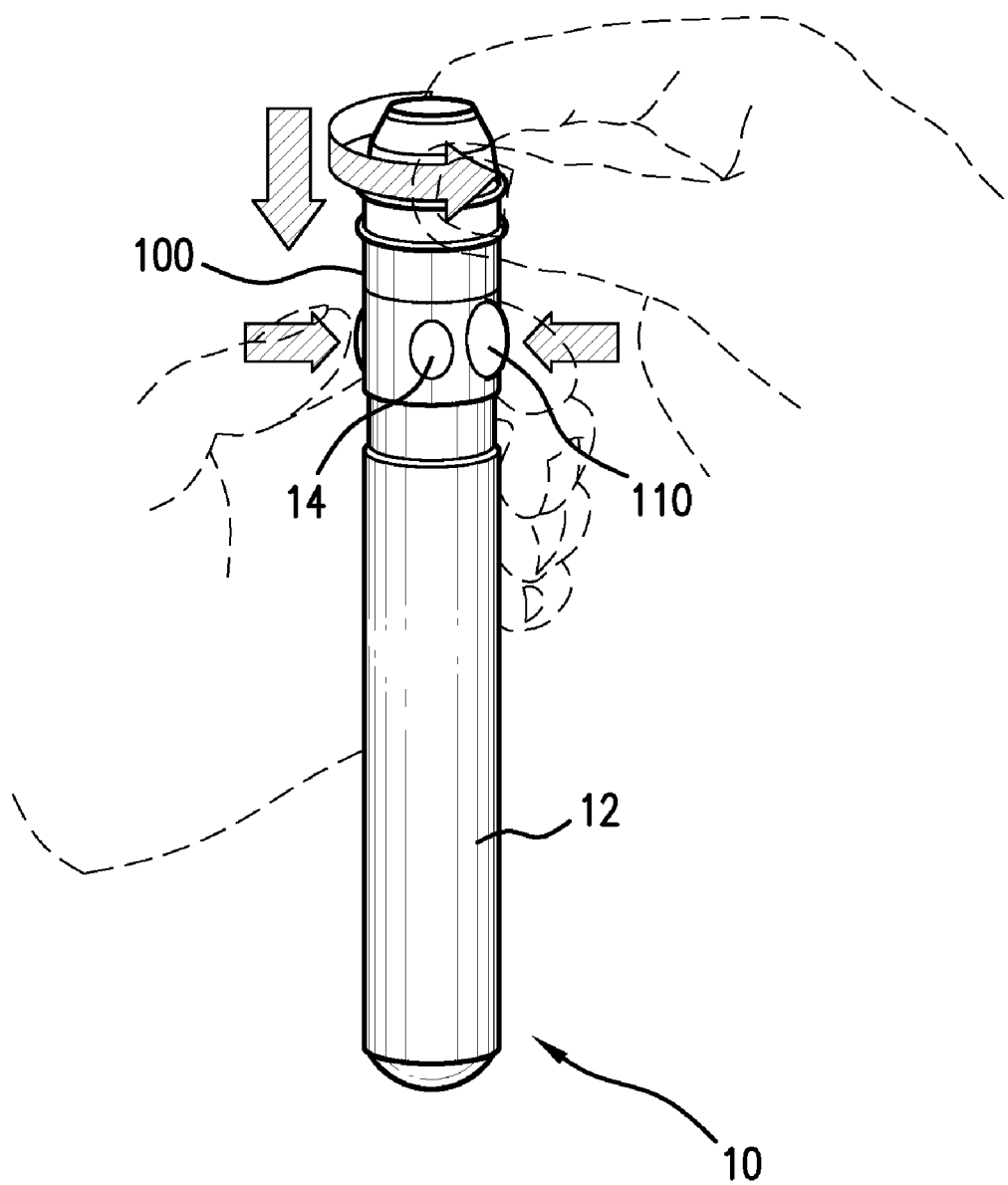
FIG. 4 is a perspective view of another embodiment of an injector device with the cap being removed.

The features of the injector 10 as described above advantageously allow the injector 10 to complete a first stage of operation, which effectively prepares the medicament and readies the injector 10 for injection. Prior to commencement of the first stage of operation, the injector 10 is preferably oriented such that the cap 100, which is in threaded association with the outer housing 12, is above the rest of the injector 10, as shown in FIG. 4. In some embodiments, a safety wrapping is affixed to the cap and the housing, the removal of which is required in order to commence the first stage of operation. Additionally, the safety wrapping can include indicia thereon to indicate that the injector should be oriented with the cap above the rest of the injector prior to commencing the first stage of operation, as well as other instructions.

In the preferred embodiment, the first stage of operation is initiated by actuation or depression of the cap lock mechanisms 110 to enable the cap 100 to be unlocked from fixed engagement with the outer housing 12. Upon actuation of the cap lock mechanisms 110, the blocking portions 112 are pivoted proximally about the pivot 113 to the release position, and thus the cap 100 is free to rotate. Upon rotation of the threads, the cap 100 moves proximally with respect to the outer housing 112, as shown in FIG. 4. Preferably, the cap 100 is able to simultaneously rotate and move proximally. Instead of threads, alternative embodiments can use other mechanisms, such as modified bayonet fittings of the cap to the housing, or by a cam mechanism. The cap 100 is preferably able to move proximally with respect to the outer housing 12 until a proximal portion of the cap 100 contacts the distal end of the engagement portions 106, which can act to limit proximal movement of the cap 100. Preferably, a quarter-turn rotation of the cap 100 is sufficient to move the cap to actuate the first stage mechanism or transfer mechanism, which in this embodiment includes cap 100, flex arm cam member 40, flex arms 44, and ram arms 48, and also to completely disengage the respective threaded surfaces 103, 107 of the engagement portions 102, 106 from threaded association with each other (e.g., rotating the cap so as to dispose the engagement portions 102 within the gaps 105 defined between the engagement portions 106, or vice versa). In other embodiments, the cap and housing can be configured to require rotation of the cap first until disengagement of the engagement portions, subsequently followed by movement of the cap proximally relative to the housing.

Figure 5:
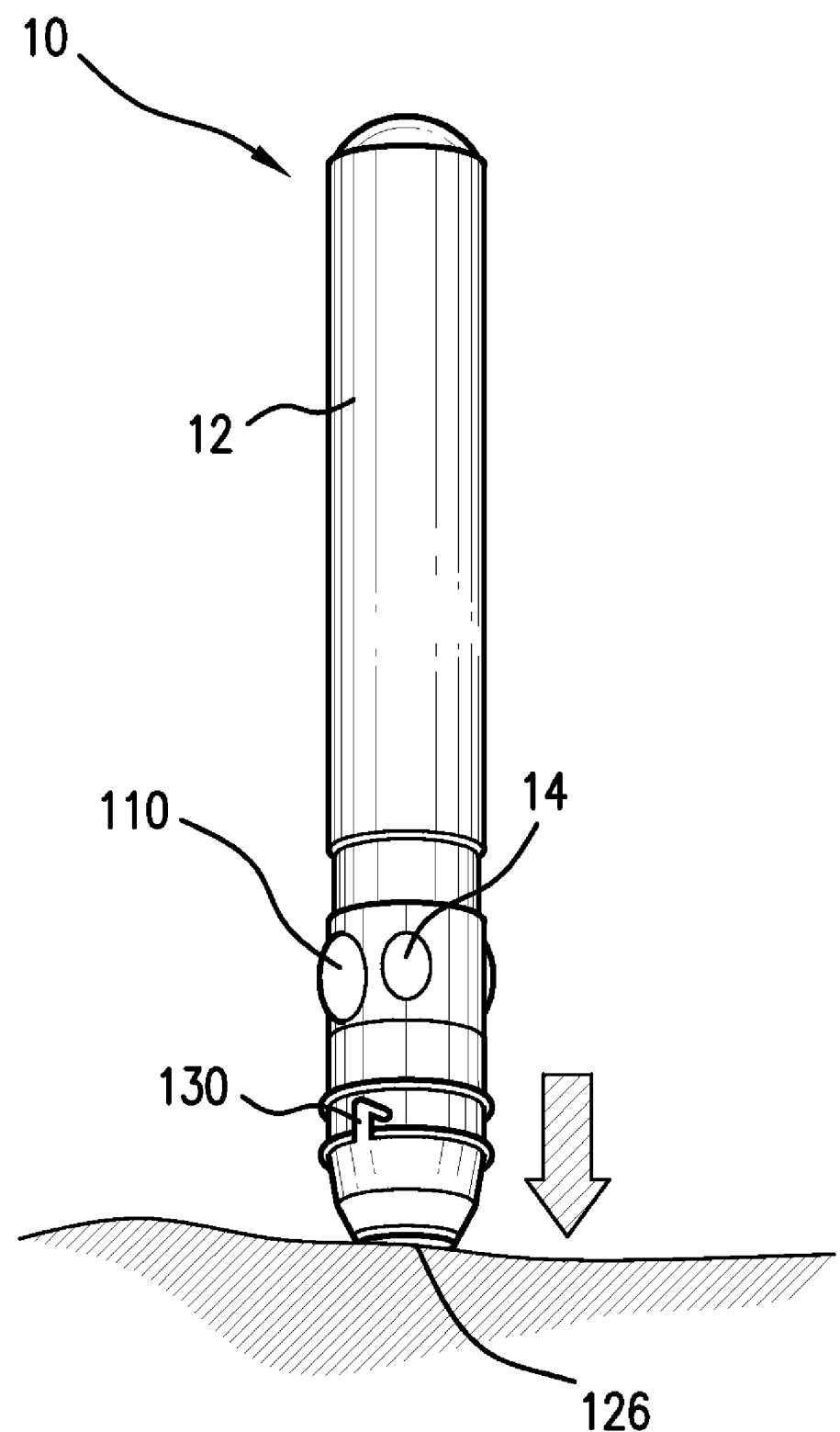
FIG. 5 is a perspective view thereof during injection.

In another embodiment, as shown in FIG. 5 for example, engagement between the cap and the outer housing is directed by a modified bayonet fitting 130 disposed on the outer housing 12. The fitting 130 includes a longitudinal slot and a lateral slot, and the cap preferably includes a cap protrusion configured to slide within the longitudinal and lateral slots. In this configuration, the cap protrusion is located at the end of the lateral slot when the cap and outer housing are engaged, and disengagement is preferably achieved by rotation of the cap such that the cap slides along the lateral slot, followed by longitudinal movement of the cap away from the outer housing such that the cap slides along the longitudinal slot to separate the cap therefrom.

In the preferred embodiment, rotation of the cap 100 with respect to the outer housing 12 disengages the engagement portions 102, 106 from threaded association with each other, thus allowing the cap 100 to be completely removed from association with the outer housing 12 by pulling the cap 100 distally away therefrom. Prior to such removal of the cap, however, movement of the cap 100 proximally with respect to the outer housing 12 also preferably initiates the first stage of operation, which preferably includes attaching the injection conduit in fluid communication with the medicament chamber 23.

For example, movement of the cap 100 in the proximal direction also moves the needle hub 124 proximally such that the needle hub 124 is received on the distal end of the medicament chamber 23 and securely mounted thereto. Preferably, the needle hub 124 has a snap-lock association with the distal end of the medicament chamber 23 that is of greater strength than the snap-lock association between the needle hub 124 and the holding area 122. Thus, the needle hub 124 will remain mounted to the distal end of the medicament chamber 23 even after removal of the cap 100 from the injector 10 by pulling the cap distally.

Additionally, upon moving the needle hub 124 proximally for mounting, the piercing end 125 of the needle 126 preferably pierces or punctures the septum 30 at the distal end of the medicament chamber 23. This puts the bore of the needle 126 in fluid communication with the medicament chamber 23 and the medicament therein, and is open at the needle tip 127 to inject the medicament therethrough. The fluid communication between the needle 126 and the medicament chamber 23 also acts to vent the chamber, thus allowing air within the chamber to escape or be released through the bore of the needle 126, such as upon movement of the plungers 28, 29 through the diluent and medicament chambers 22, 23. Orientation of the injector 10 with the cap 100 above the injector 10 advantageously facilitates efficient venting of the medicament chamber 23, without the medicament leaking from the needle hub 124.

Movement of the cap 100 in the proximal direction also causes a proximal side 80 of cap 100 to contact and push the base 41 of the flex arm cam member 40. Upon engagement by the proximal side 80, the flex arm cam member 40 is also moved in the proximal direction, sliding the flex arm cams 42 proximally along and against the distal portions of the flex arms 44. The flex arm cams 42 thus cam the flexible flex arms 44 radially inwardly from the blocking position to the release position with respect to the ram arms 48. Because the flex arms 44 in the release position are no longer longitudinally aligned with the ram arms 48, the spring 62 is able to move the ram 60 in the distal direction until the enlarged end 64 reaches aperture 58, where the trigger protrusions 56 prevent further distal movement of the ram 60. In the first stage operation, the ram 60 preferably moves longitudinally by a predetermined first amount, which is less than full travel. As the ram 60 moves distally, the ram arms 48 also slide distally radially over the flex arms 44, and the distal portions of the ram arms 48 are received within slots 43 between the flex arm cams 42.

Movement of the ram 60 distally also moves the first plunger 28 in the distal direction, pushing the diluent in the diluent chamber 22, which pushes the second plunger 29 in the distal direction until second plunger 29 reaches the reconstitution bulge 32. When the second plunger 29 enters the reconstitution bulge 32, a fluid passageway is created between the diluent chamber 22 and the medicament chamber 23, allowing diluent from the diluent chamber 22 to enter and mix with the medicament in the medicament chamber 23 as the diluent chamber 22 is reduced in volume because the first plunger 28 continues to move towards the second plunger 29. Preferably, the first stage mechanism is configured to move the first plunger 28 until contacting second plunger 29 in the bulge 32, but lesser or greater movement can be suitable in some embodiments.

Further mixing of the diluent and medicament in the medicament chamber 23 to suspend or dissolve the medicament in the diluent can be accomplished by shaking of the injector 10. In some embodiments, for example the embodiment shown in FIGS. 4 and 5, the outer housing 12 can include a transparent window portion 14 adjacent the medicament chamber 23 such that the user can physically inspect the extent of mixing of the suspension through the window.

At this point, the first stage of operation is completed and the injector 10 is ready for injection of the mixed medicament from the medicament chamber 23. Injection is preferably achieved by completion of a second stage of operation, which uses a second stage mechanism or firing mechanism that includes guard 66, trigger mechanism 52, and ram 60 in this embodiment. The user-operable trigger device to activate the device in both first and second stages of operation can include a single control that is operated in first and second triggering stages, or, as in the preferred embodiments described, can include separate user-manipulable controls that are operated separately from each other. For example, the control to initiate the second stage can be operable once the first stage is completed, but with the second stage mechanism keeping the injector from firing prior to its activation.

The injector 10 includes a trigger mechanism 52 that is preferably housed within the proximal end of the outer housing 12. The trigger mechanism 52 includes a portion of the inner portion or housing 13 that can be attached to the outer housing 12, such as by snaps, an adhesive, a weld, or other known attachment. Trigger protrusions 56 extend radially inwardly from the proximal end of trigger arms 57 and are resiliently biased outwardly. Trigger protrusions 56 form the aperture 58 about the shaft 63 of the ram 60, the shaft 63 being received in the aperture 58. The shaft 63 is preferably at least as long as the longitudinal movement of the ram 60 required in the first stage of operation. Upon movement of the ram 60 in the distal direction during the first stage of operation, the trigger protrusions 56 enter into blocking association with the enlarged end 64 of the ram 60 to prevent further distal movement of the ram 60 prior to the firing of the injector 10 upon actuation of the trigger mechanism 52.

A trigger member of the trigger mechanism 52, such as a latch portion or housing 61, is provided exterior to the inner housing 13 to retain the trigger protrusions 56 in the blocking association with the enlarged end 64 after the first stage of operation to prevent premature firing of the injector 10. The latch housing 61 is slideable inside the outer housing 12 with respect to the inner housing 13, preferably in an axial direction, and the latch housing 61 preferably surrounds the inner housing 13.

The distal end of the outer housing 12 preferably includes a needle guard 66 that is moveable with respect to the outer housing 12. The needle guard 66 is retractable between a protecting position and an injecting position. In the protecting position, the needle 126 is disposed within the guard 66. The needle guard 66 is retractable, preferably into the outer housing 12, in a proximal direction to the injecting position, in which the injection portion 127 of the needle 126 is exposed for insertion into a patient. In the preferred embodiment, the proximal movement of the guard is prevented substantially in the injecting position. The guard 66 is preferably resiliently biased distally towards the protecting position by compression coil spring 72. Also, the needle guard 66 has an axial opening 74 to allow the needle 126 pass there through, and which may be sized according to the type of injector desired. The needle guard 66 extends proximally through the injector 10 and is of unitary with the latch housing 61.

Other embodiments can incorporate alternative trigger mechanisms for actuating firing of the injector. For example, the injector can include a button or other suitable depressible member on the outer housing that, upon depression thereof, actuates firing of the injector.

In the preferred embodiment, the second stage of operation to fire the injector 10 is initiated by retracting the guard 66 to the injecting position, such as by pushing the guard against the patient's skin. The needle guard 66 is associated with the latch housing 61 such that when the guard 66 is displaced proximally, it slides the latch housing 61 also in a proximal direction to release the trigger protrusions 56 from blocking association with the enlarged end 64 of the ram 60. Preferably, the latch housing 61 has a latching portion that abuts the inner housing 13 in an association to bias and maintain the trigger protrusions 56 positioned in the blocking association with the enlarged end 64 prior to the firing of the injector 10. When the latch housing 61 is slid proximally by the retracting of the guard 66 to the injecting position, the latching portion slides beyond the portion of inner housing 13 that it contacts to flex the trigger protrusions 56, allowing the trigger protrusions 56 to move radially outwardly with respect to the shaft 63 and therefore from the blocking association with the enlarged end 64. When this happens, i.e., when the trigger mechanism 52 is actuated, the spring 62 biases the ram 60 against the first plunger 28 to fire the injector 10. The cartridge 18 is configured such that when the first plunger 28 is displaced in a distal direction, the volume of the medicament chamber 23 is decreased, forcing the mixed medicament out therefrom and through the bore of needle 24. Latch housing 61 preferably defines trigger openings adjacent to the latching portions, which are configured to receive a portion of the inner housing 13, such as the surface disposed radially outwardly from the trigger protrusions 56. A same energy source, such as spring 62, can be configured to power both first and second stages.

In the preferred embodiment, the user can push the distal end of the injector 10 against the patient's skin as shown in FIG. 5, pushing the needle 126 into the skin at the injection location, preferably substantially at the same speed as the injector is pushed, although alternative embodiments can move the cartridge forward to insert the needle. Once the needle 126 is fully inserted to an insertion point at a penetration depth in the patient's skin, the trigger mechanism 52 fires the injection of medicament into an injection location.

Preferably, the injecting position of the guard 66 is such that a predetermined length of the end of needle 126 is exposed from the guard 66. In some embodiments, such as where the opening 74 is of a sufficiently large diameter, the skin of the patient maybe allowed to extend into the opening 74 when the device 10 is pressed there against, and a needle that does not protrude beyond the distal end of the guard 66 can be used. In most embodiments, the distance by which the needle tip extends past the distal end of the guard will be fairly close to the depth of the insertion of the needle. Additionally, in some embodiments, the distal surface of the guard can be discontinuous.

The injector 10 can be configured for various types of subcutaneous injections, intradermal injections, intravascular injections, or other types of injections. In the preferred embodiment, the guard 66 is configured to allow insertion of the needle to a penetration depth in the skin that is up to about 5 mm below the skin surface. More preferably, the penetration depth is less than about 4 mm, and in one embodiment is less than about 3 mm. Preferably, the insertion depth is at least about 0.5 mm and more preferably at least about 1 mm. In another embodiment, the distance by which the needle extends past the guard 66 or the distal surface of the guard 66 that contacts the skin is up to about 5 mm, more preferably up to about 4 mm, and in one embodiment up to about 3 mm. Preferably, extension distance is at least about 0.5 mm, more preferably at least about 1 mm, and most preferably at least about 2 mm. In a preferred embodiment, tip 127 of the needle 126 extends by a distance of around 2.5 mm beyond the portion of the guard 66 that contacts the skin in the injecting position. In alternative embodiments, the needle tip stops behind or proximal to the guard, and penetrates the skin that is pushed into the guard.

In another embodiment, such as for intramuscular injection, the injector is configured to allow the needle to be inserted into the patient to a penetration depth in the skin, or alternatively beyond the distal surface of the guard, by a distance of up to about 15 mm. In one embodiment, this distance is about between 10 mm and 14 mm. In an embodiment for jet injection of epinephrine for instance, a preferred penetration depth or distance beyond the guard is between about 12 mm and 13.5 mm, and most preferably around 12.7 mm. Jet injection with this length needle improves the distribution of the medicament in the patient tissue compared to non-jet injection. Other exposed needle lengths can be selected for jet injection to different depths below the skin, with a preferred overall penetration length of between about 0.5 mm and about 20 mm. In these embodiments, the needle guard is preferably configured for retracting from a protecting position, preferably covering the entire needle, to an injecting position, in which the desired length of the end of the needle is exposed.

In some embodiments, the energy source, which is preferably spring 62, and the container, which is preferably cartridge 18, are configured to jet inject the medicament into the patient to an injection site. The spring 62 applies a force on the ram 60 to bias the first plunger 28 that is preferably sufficient to elevate the pressure within the diluent and medicament chambers 22, 23 to a level high enough to eject the medicament from the needle 126 as a jet. Jet injection is to be understood as an injection with sufficient velocity and force to drive the medicament to locations remote from the needle tip 127. The jet injector embodiments deliver a jet injection, the medicament is jet injected distally or in other directions, such as generally radially by the elevated pressure jet, which beneficially improves the distribution of the medicament after the injection and keeps a large bolus from forming that can detrimentally force the medicament to leak back out of the patient around the needle or through the hole left behind by the needle after it is removed. In alternative autoinjector embodiments that use needles, the injection pressures are relatively very low, and the medicament exits the needle tip inside the patient and is typically deposited locally around the needle in a bolus.

Preferably, the needle 127 is between 26 and 28 gage, and are most preferably around 27 gage, but alternatively other needle gages can be used where the other components are cooperatively configured to produce the desired injection. Preferably, the components of the injector 10 are configured to jet inject the medicament to a subterraneous injection site.

Preferred injection rates are below about 0.75 mL/sec., more preferably below about 0.6 mL/sec., and preferably at least about 0.2 mL/sec., more preferably at least about 0.3 mL/sec, and most preferably at least about 0.4 mL/sec. Preferably, the injection of the entire amount of medicament is completed in less than about 4 seconds, more preferably in less than about 3 seconds, and most preferably in less than about 2.5 seconds. Preferably, the medicament injection takes at least about 1 second, and more preferably at least 1.5 seconds, and most preferably at least about 1.75 seconds. A preferred embodiment injects the medicament at about 0.5 mL/sec., completing the injection of 1 mL in about 2 seconds.

The entire amount of mixed medicament contained and injected from the container 18 is preferably between about 0.02 mL and 4 mL, and preferably less than about 3 mL, and in the preferred embodiment is around 1 mL. Larger volumes may also be selected depending on the particular medicament and dosage required. Preferably, the cartridge 18 shown in FIG. 1 is assembled into the remaining parts of the injector 10 already containing the desired amount of diluent and medicament therein. In a preferred embodiment, the container 18 contains about 1 mL of diluent and medicament.

While illustrative embodiments of the invention are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present invention.

What is claimed is:

1. An injector for injecting a medicament into a patient, comprising:
   a transfer and firing device associable with a container that defines a first and second chambers, the transfer and firing device being operable to transfer a fluid from the first chamber to the second chamber in a first stage of operation and being operable for firing the fluid from the second chamber through an injection conduit, associated with the container, in a second stage of operation;
   a trigger device configured to block operation of the transfer and firing device to end the first stage of operation, the trigger device in blocking association with the transfer and firing device is operable manually in a second triggering stage which causes a firing mechanism to initiate the second stage of operation; and
   a transfer control that is manually operable to initiate operation of the transfer and firing device in the first stage of operation,
   wherein the injection conduit has a position that is fluidly incommunicated with the second chamber, the transfer and firing device configured to fluidly communicate the injection conduit with the second chamber in the first stage of operation,
   wherein the injection conduit comprises a communicating needle portion, the transfer control operable to relatively move the communicating needle portion with respect to the second chamber to pierce the container to fluidly communicate the second chamber with the communicating needle portion in the first stage of operation.

2. An injector for injecting a medicament into a patient, comprising:
   a transfer and firing device associable with a container that defines a first and second chambers, the transfer and firing device being operable to transfer a fluid from the first chamber to the second chamber in a first stage of operation and being operable for firing the fluid from the second chamber through an injection conduit, associated with the container, in a second stage of operation;
   a trigger device configured to block operation of the transfer and firing device to end the first stage of operation, the trigger device in blocking association with the transfer and firing device is operable manually in a second triggering stage which causes a firing mechanism to initiate the second stage of operation; and
   a transfer control that is manually operable to initiate operation of the transfer and firing device in the first stage of operation
   wherein the transfer control comprises a cap disposed for covering the injection conduit and being associated with the transfer and firing device such that removal of the cap from covering the injection conduit initiates the first stage of operation of the transfer mechanism.

3. The injector of claim 1 or 2, wherein the transfer and firing device comprises a firing ram that is movable over a first throw in the first stage of operation and a second throw in the second stage of operation and causes moves the fluid from the first chamber to the second chamber in the first stage of operation and from the second chamber through the injection conduit in the second stage of operation.

4. The injector of claim 3, wherein the trigger device is configured to block movement of the ram beyond the first throw, the trigger device being actuatable to release the ram to travel over the second throw.

5. The injector of claim 1 or 2, further comprising a retractable guard that is movable between:
a protecting position in which the injection conduit is disposed within the guard; and
an injecting position in which an injection needle portion of the injection conduit is exposed for injection of the fluid in the patient;
wherein the trigger device is configured for operating the transfer and firing device in the second stage after the retractable guard is retracted from the protecting position.

6. The injector of claim 5, wherein the retractable guard is operably associated with the device to cause an injection trigger mechanism to operate the firing mechanism when the guard is retracted to the injecting position.

7. The injector of claim 1 or 2, wherein the injection conduit comprises an injecting needle portion disposed and configured to pierce the skin of the patient for assisting the injection of the fluid in the second stage.

8. The injector of claim 7, wherein the transfer and firing device are configured for delivering the fluid by jet injection to an injection site within the patient tissue remote from the injecting needle.

9. The injector of claim 1, wherein the transfer control comprises a cap associated with the container and disposed to cover the injection conduit prior to the first stage of operation, wherein the cap is configured such that removal of the cap from covering the injection conduit initiates the first stage of operation.

10. The injector of claim 9, further comprising a cap release in locking association with the cap to prevent operation thereof, and being positionable in a release position in which the cap release releases the cap to permit operation thereof in the first stage of operation.

11. The injector of claim 1 or 2, wherein the second chamber comprises a medicament, and the fluid comprises a diluent configured for dissolving or suspending the medicament therein for injection into the patient.

12. The injector of claim 1 or 2, further comprising the injection conduit and the container, which container contains the fluid in the first chamber and is associated with the injection conduit for injecting the fluid therethrough in the second stage of operation.

13. The injector of claim 1 or 2, further comprising an energy source in powering association with the transfer and firing device to drive the transfer and firing device in both the first and second stages.

14. The injector of claim 2, wherein the injection conduit has a position that is fluidly incommunicated with the second chamber, the transfer and firing device configured and to fluidly communicate the injection conduit with the second chamber in the first stage of operation.

15. The injector of claim 14, further comprising a transfer control that is manually operable to initiate operation of the transfer and firing device in the first stage of operation, wherein the injection conduit comprises a communicating needle portion, the transfer control operable to relatively move the communicating needle portion with respect to the second chamber to pierce the container to fluidly communicate the second chamber with the communicating needle portion in the first stage of operation.

16. The injector of claim 15, wherein the injection conduit comprises an injecting needle portion disposed and configured to pierce the skin of the patient for assisting the injection of the fluid in the second stage.

17. The injector of claim 16, wherein the transfer and firing device are configured for delivering the fluid by jet injection to an injection site within the patient tissue remote from the injecting needle.

18. The injector of claim 15, further comprising a cap release in locking association with the cap to prevent operation thereof, and being positionable in a release position in which the cap release releases the cap to permit operation thereof in the first stage of operation.

19. An injector for injecting a medicament into a patient, comprising: a transfer mechanism associable with a container that defines a first and second chambers, the transfer mechanism operable by a user to transfer a fluid from the first chamber to the second chamber in a first stage of operation;
a cap disposed for covering an injection conduit that is associated with the container, the cap being associated with the transfer mechanism such that a movement of the cap initiates the first stage of operation of the transfer mechanism; and
a firing mechanism operable by the user for firing the fluid from the second chamber through the injection conduit in a second stage of operation;
wherein the firing mechanism includes a needle guard that has a protective position disposed for covering a needle of the injection conduit, and an injecting position exposing the needle, and the cap covering the injection conduit covers the needle and needle guard;
wherein the needle guard is configured for causing the firing mechanism to fire the fluid when moved to the retracted position.

20. An injector for injecting a medicament into a patient, comprising:
a transfer mechanism associable with a container that defines a first and second chambers, the transfer mechanism operable by a user to transfer a fluid from the first chamber to the second chamber in a first stage of operation;
a cap disposed for covering an injection conduit that is associated with the container, the cap being associated with the transfer mechanism such that a movement of the cap initiates the first stage of operation of the transfer mechanism;
a firing mechanism operable by the user for firing the fluid from the second chamber through the injection conduit in a second stage of operation; and
a housing associated with the cap such that rotation of the cap with respect to the housing causes proximal movement of the cap with respect thereto, the cap being configured such that the proximal movement thereof initiates the first stage of operation;
wherein at least the housing or the cap has a partial thread in threaded engagement with the other such that a partial rotation of the cap with respect to the housing causes said proximal movement of the cap that initiates the first stage of operation, and further rotation of the cap releases the threaded engagement for releasing the cap from the housing.

21. The injector of claim 19 or 20, wherein:
the cap is retained covering the injection conduit until the transfer mechanism is operated in the first stage of operation, and the cap is separable from the injection conduit once the transfer mechanism is operated in the first stage of operation.

22. The injector of claim 21, wherein the injection conduit comprises a communicating needle portion, a transfer control being operable to relatively move the communicating needle portion with respect to the fluid chamber to pierce the container adjacent a needle hub to fluidly communicate the fluid chamber with the communicating needle portion.

23. The injector of claim 19, further comprising the injection conduit, which includes the needle.

24. The injector of claim 19 or 20, further comprising the container, which contains the fluid in the first chamber.

25. The injector of claim 24, wherein:
the injection conduit comprises a needle;
firing mechanism includes a needle guard that has a protective position covering the needle, and an injecting position exposing the needle; and
the cap covering the injection conduit covers the needle and needle guard.

26. The injector of claim 19, wherein the cap is configured such that proximal movement of the cap, opposite a direction of the firing of the fluid, initiates the first stage of operation.

27. The injector of claim 19, further comprising a housing associated with the cap such that rotation of the cap with respect to the housing causes proximal movement of the cap with respect thereto, the cap being configured such that the proximal movement thereof initiates the first stage of operation.

28. The injector of claim 19 or 20, wherein said movement of the cap comprises a removal of the cap from covering the injection conduit.

29. The injector of claim 19 or 20, further comprising an energy source in powering association with the transfer and firing mechanisms to drive transfer and firing mechanisms in both the first and second stages.

30. The injector of claim 19 or 20, further comprising an injection trigger mechanism operably associated with the firing mechanism to operate the firing mechanism to initiate the second stage.

31. The injector of claim 20, wherein:
the firing mechanism includes a needle guard that has a protective position disposed for covering a needle of the injection conduit, and an injecting position exposing the needle; and the cap covering the injection conduit covers the needle and needle guard.

32. The injector of claim 31, further comprising the injection conduit, which includes the needle.

33. The injector of claim 31, wherein the needle guard is configured for causing the firing mechanism to fire of the fluid when moved to the refracted position.

* * * * *